United States Patent [19]

Eckerle

[11] Patent Number: 5,289,823
[45] Date of Patent: Mar. 1, 1994

[54] NON-INVASIVE AORTIC BLOOD FLOW SENSOR AND METHOD FOR NON-INVASIVELY MEASURING AORTIC BLOOD FLOW

[75] Inventor: Joseph S. Eckerle, Redwood City, Calif.

[73] Assignee: Colin Electronics Co., Ltd., Aichi, Japan

[21] Appl. No.: 881,756

[22] Filed: May 12, 1992

[51] Int. Cl.⁵ ............................................. A61B 5/00
[52] U.S. Cl. .................................. 128/679; 128/691; 128/672
[58] Field of Search ........ 128/672, 666, 679, 687–691, 128/748

[56] References Cited

U.S. PATENT DOCUMENTS

| | | |
|---|---|---|
| 3,926,179 | 12/1975 | Petzke et al. |
| 4,423,738 | 1/1984 | Newgard |
| 4,465,063 | 8/1984 | Nielsen et al. |
| 4,718,426 | 1/1988 | Russell |
| 4,722,347 | 2/1988 | Abrams et al. |
| 4,802,488 | 2/1989 | Eckerle |
| 4,802,490 | 2/1989 | Johnston |
| 4,807,638 | 2/1989 | Sramek |
| 4,877,035 | 10/1989 | Bogen et al. |
| 4,905,704 | 3/1990 | Walloch |
| 4,949,724 | 8/1990 | Mahutte et al. |
| 4,987,900 | 1/1991 | Eckerle et al. |
| 4,993,420 | 2/1991 | Welkowitz et al. ............... 128/691 |
| 5,005,581 | 4/1992 | Honeyager |
| 5,048,533 | 9/1991 | Muz ..................................... 128/679 |

Primary Examiner—Lee S. Cohen
Assistant Examiner—Robert L. Nasser, Jr.
Attorney, Agent, or Firm—Oliff & Berridge

[57] ABSTRACT

A non-invasive aortic blood flow sensor is disclosed. The sensor determines the blood flow in the aorta of a patient based on the pressure difference between the right and left subclavian arteries. The pressure of the subclavian arteries is non-invasively measured by determining the blood pressures in the arteries of the patient's right and left arms by means of tonometric blood pressure sensors. The signals from the tonometric sensors are first equalized to account for any pressure waveform distortion due to propagation of the pulse from the aorta to the sensor locations. Next, a correction is made for DC offset. The modified pressure signals are then compared, and the pressure difference determined. The blood flow is determined from the pressure difference by known pressure/flow relationships.

30 Claims, 4 Drawing Sheets

NON-INVASIVE AORTIC BLOOD FLOW SENSOR AND METHOD FOR NON-INVASIVELY MEASURING AORTIC BLOOD FLOW

BACKGROUND OF THE INVENTION

1. Field of the Invention

The present invention relates generally to an apparatus and method for non-invasively measuring aortic blood flow in a patient. More particularly, the invention relates to an apparatus and method for determining aortic blood flow by measuring the pressure differential between the left and right subclavian arteries.

2. Description of the Related Art

In a conventional flow apparatus and method, aortic blood flow is measured by one of several techniques that involve injection of a "bolus" of foreign material into the ventricle of the heart or into the aorta. The movement of the "bolus" is then monitored by thermal or nuclear (x-ray, gamma ray) sensors. All of these techniques have the severe disadvantage of being invasive. The foreign material injected is usually harmless, but some patients may have adverse reactions to it. These procedures usually must be performed in a "cath lab", which is a relatively expensive facility. This, in addition to the need for the services of a skilled cardiologist, make these procedures relatively expensive.

An alternative conventional apparatus and method uses ultrasonic imaging techniques to measure the blood flow velocity profile in the aorta. Total volumetric blood flow can be found by integration of the velocity profile. However, this method is very sensitive to movement artifacts. The equipment is also too large and sensitive to movements to be used on an ambulatory patient, or during surgery. The equipment is also relatively expensive.

SUMMARY OF THE INVENTION

A general object of the invention is to provide an improved method and apparatus for non-invasive measurement of blood flow in the aorta.

A second object is to provide simultaneous, non-invasive measurement of aortic blood flow and blood pressure.

A third object is to provide a non-invasive measurement of cardiac output.

A fourth object is to provide a method and an apparatus to accomplish the above objects more cost-effectively than conventional methods and apparatuses.

A fifth object is to provide a method and an apparatus to accomplish the above objects which is more resistant to movement artifacts.

A sixth object is to provide an improved method and apparatus for measurement of blood pressure, cardiac output, and other cardiovascular parameters during an exercise stress test.

A seventh object is to measure cardiac output with an apparatus that is practical for routine use in clinical anesthesia.

The present invention overcomes several shortcomings of conventional aortic blood flow measurement apparatuses and methods. It is completely non-invasive. The apparatus is relatively small, lightweight, and inexpensive. The apparatus comprises one small sensor attached to each of the patient's wrists. No sensors are placed on or near the patient's chest. Thus, the method and apparatus of the present invention may be used during thoracic surgery and heart massage to monitor cardiac output in real time.

BRIEF DESCRIPTION OF THE DRAWINGS

The preferred embodiments will be described with reference to the drawings, in which the elements have been denoted by like reference numerals throughout the figures, and in which.

DETAILED DESCRIPTION OF THE PREFERRED EMBODIMENTS

Figure 1:
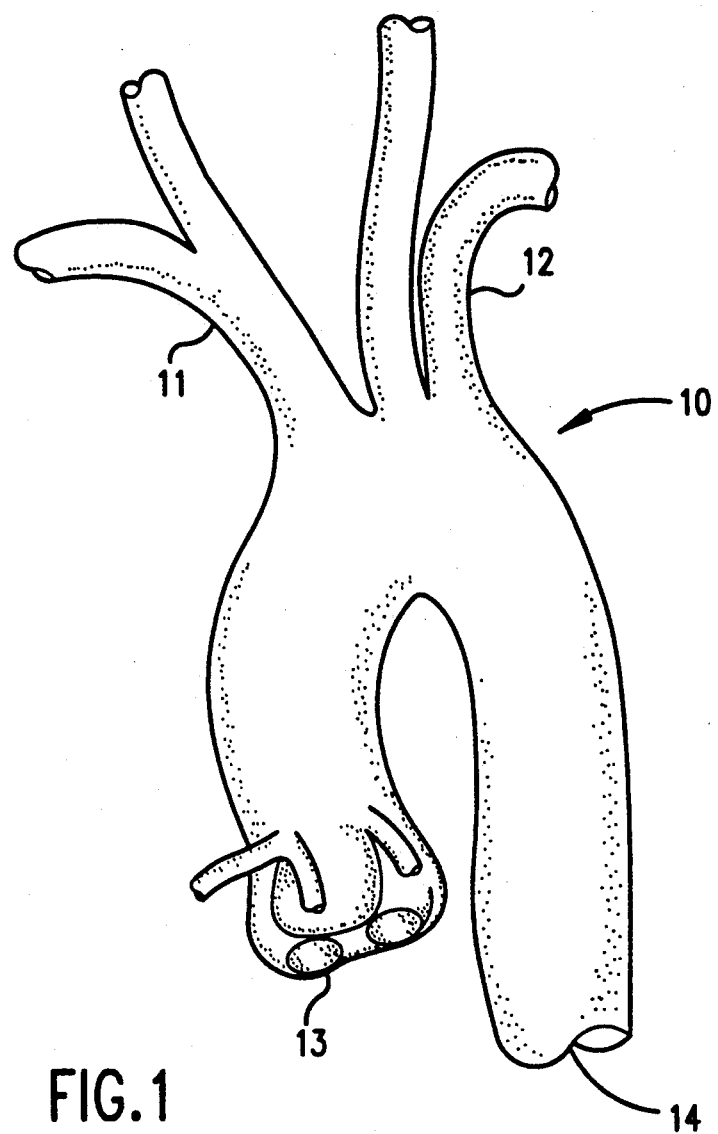
FIG. 1 is a ventral view of an aorta.

The anatomy of the aortic arch 10 and, in particular, of the subclavian arteries 11 and 12, is shown in FIG. 1. Blood ejected by the left ventricle of the heart enters the arch at its proximate end 13. Blood destined for the legs and torso exits the arch at its distal end 14. As shown in this illustration, the right subclavian artery is located on the aortic arch 10 about 2 or 3 cm "upstream" of the left subclavian artery 12. This 2-cm section of the aorta, together with the two subclavian arteries, can be used to form a capillary-(or orifice-) type flowmeter.

Figure 2:
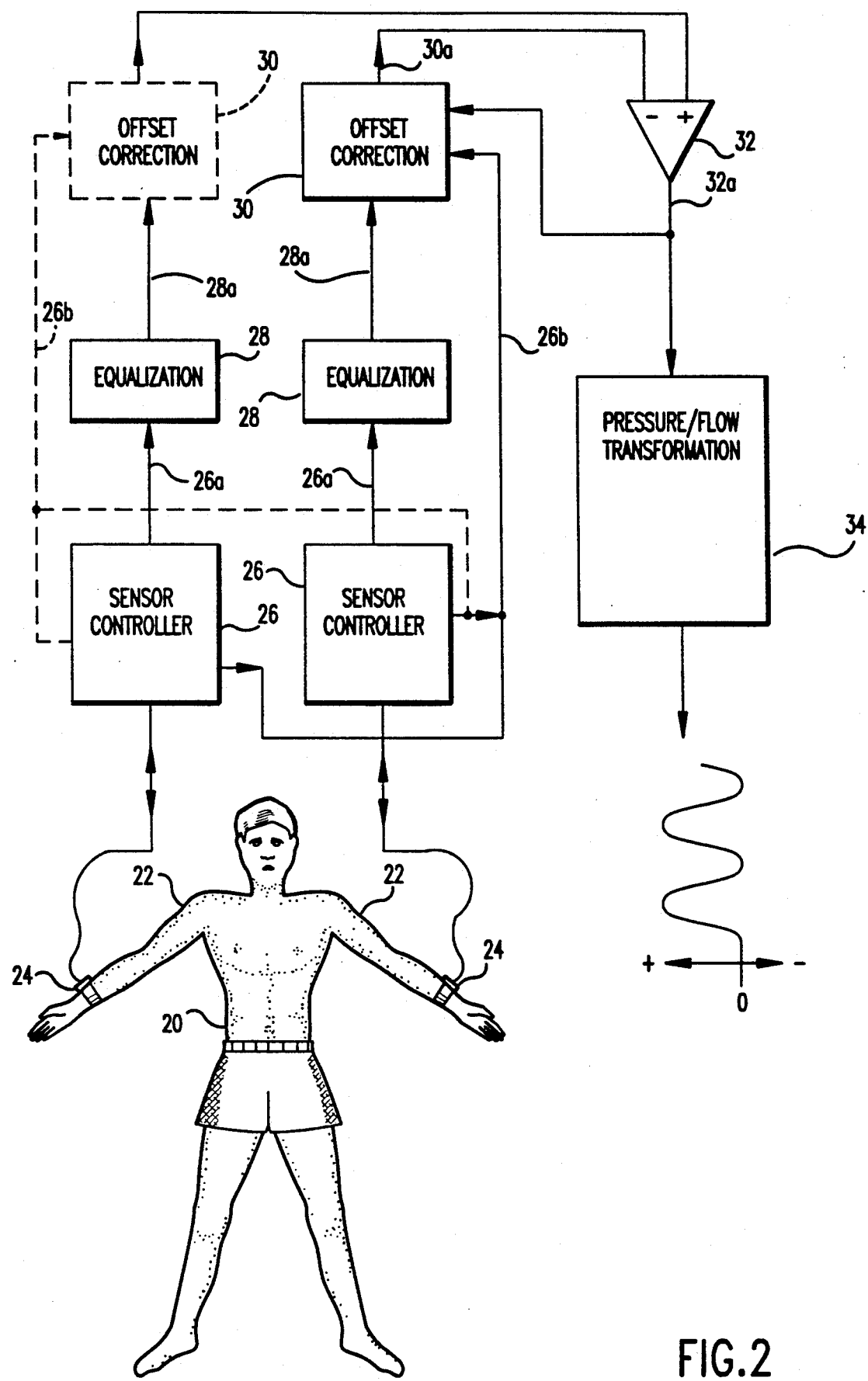
FIG. 2 is a schematic view of the apparatus of the present invention.

Specifically, the subclavian artery pressures are measured indirectly by means of arterial blood pressure sensors placed on arteries of the arms 22 of a patient 20, as shown in FIG. 2. The brachial arteries, radial arteries, ulnar arteries or even finger arteries can be used. Likewise, any known blood pressure sensor can be used. However, in the preferred embodiment, a tonometer-type blood pressure sensor 24 is applied to the radial artery of each arm 22.

The difference between the two subclavian artery pressures is directly related to the instantaneous blood flow in the aortic arch 10. Thus, the aortic arch 10 is used as the flow-to-pressure transducer of a capillary-type flowmeter. It is arguable that the configuration is more similar to an orifice-type flowmeter. However, this is merely a semantic distinction.

FIG. 2 shows the preferred embodiment of the apparatus of the present invention for aortic blood flow measurement in schematic form. As shown in FIG. 2, an arterial tonometer blood pressure sensor 24 is applied to each wrist of the patient 20 to measure pressure in the left and right radial arteries. A blood pressure cuff (not shown) may optionally be used on one or both of the patient's arms 22 for determination of coefficients to be used in signal processing software of the tonometry system, emergency blood pressure measurements, and other purposes. The apparatus of the preferred embodiment includes two sensor control means 26. Each sensor control means 26 typically comprises one or more microprocessors and "DSP chips" and is connected to one tonometer sensor 24. Each sensor control means 26 processes the sensor signals, positions the sensor 24, adjusts the hold-down pressure (HDP) of the sensor 24 against the patient's wrist, applies calibration (if any) to the sensor signals, and outputs a signal 26a representing the instantaneous blood pressure in one of the radial arteries. These are functions used in arterial tonometry and are shown, for example in U.S. Pat. Nos. 4,836,213 and 4,987,900.

Each radial arterial blood pressure signal is subjected to further processing prior to final display, as shown in FIG. 2. First, each blood pressure signal 26a is output by one of the sensor control means 26 to a corresponding equalization device 28. Each equalization device 28 models the inverse of the transfer function between the pressure at the aortic anastomosis of the left or right subclavian artery and the sensor location on the corresponding radial artery. Since the vasculature of the two arms is very similar, the two equalization devices 28 will generally have similar transfer functions, but they need not be identical. These transfer functions may be may be tailored to each individual patient 20 based on age, weight, and other factors. After processing by the corresponding equalization device 28, each equalized signal 28a may be output to a corresponding offset correction device 30 or may be output directly to a differential amplifier 32. Each offset correction device 30 (described in detail below) corrects for small inaccuracies in the flow signal that would be caused by any "DC offset" between the two sensor signals.

Each signal output by either the corresponding offset correction device 30 or the corresponding equalization device 28 is input to one input terminal of the differential amplifier 32. The differential amplifier 32 generates a difference signal 32a equal to the amplified difference between the two input signals. The difference signal 32a is roughly proportional to the instantaneous blood flow in the aortic arch 10.

The difference signal 32a output by the differential amplifier 32 is input to a pressure-to-flow transformation device 34. This transformation device 34 can be implemented with a microprocessor or "DSP chip" and converts the difference signal, which represents the pressure drop in the 2-cm section of the aorta 10 between the right and left subclavian arteries 11 and 12, to the flow signal, which represents the instantaneous flow rate of blood in that 2-cm section.

The transformation device 34 is well-known to those skilled in the art of flowmeters. For example, for an orifice-type flow sensor, flow is related to pressure by:

$$q = C\sqrt{(P_1 - P_2)}, \quad (1)$$

where q is the flow, C is a coefficient (fixed for a given fluid and flowmeter), $P_2$ is the pressure downstream of the flow sensor, and $P_1$ is the pressure upstream of the sensor. For this type of flow sensor, the pressure-to-flow transformation device 34 simply implements the equation, $$q = C\sqrt{\Delta P} \quad (2)$$

where $\Delta P$ represents the input to the device 32a $(P_1 - P_2)$.

While the behavior of the aortic arch 10 will be more complex than that of a simple, orifice-type flow sensor, the overall method and means for determining flow based on a pressure difference that is monotonically and directly related to the flow is identical. The present invention exploits this behavior to determine aortic blood flow from the easily measured pressure difference between the two subclavian arteries 11 and 12.

At low flow rates, the flow will be laminar, and the pressure drop, $\Delta P$, is directly proportional to flow. This regime is known as Hagen-Poiseuille flow. The rate of change in pressure per unit length, dp/dx is:

$$\frac{dp}{dx} = \frac{-8\mu V}{r_o^2} \quad (3)$$

where V is the average blood velocity, $\mu$ is the viscosity of the blood, and $r_o$ is the internal radius of the aorta 10.

This expression may be rewritten for the pressure drop, $\Delta P$, generated by flow through a vessel of length, $\Delta X$, as follows:

$$\Delta P = \frac{-8\mu V \Delta X}{r_o^2}. \quad (4)$$

An expression for the blood flow rate q, integrated over cross-section of the aorta 10, is:

$$q = \pi r_o^2 \rho V, \quad (5)$$

where $\rho$ is the blood density. Now, substituting V from Eq. (5) into Eq. (4) and rearranging gives:

$$q = \frac{-\rho \pi r_o^4}{8\mu \Delta x} \Delta P. \quad (6)$$

Thus, the laminar blood flow rate q is directly proportional to the pressure drop $\Delta P$, and the proportionality constant is composed of parameters that are essentially fixed for a given patient. In the aorta 10, $\Delta x$ is the distance—about 2 cm—between the anastomoses of the two subclavian arteries 11 and 12. The laminar flow relationship given in Eq. (6) holds only for relatively-low flow velocities, up to a Reynold's number, Re, of about 1,000 to 5,000. The line 38 shown in FIG. 4 graphically represents the laminar flow region defined by Eq. (6).

At relatively high flow velocities, the flow is turbulent. In this regime, the friction factor, f, will asymptotically approach a constant value, which depends on the roughness of the aortic walls. The friction factor f $$f = \frac{\Delta P}{4(L/D)(\rho V^2/2)} \quad (7)$$

where $\Delta P$ is the pressure drop between the two measurement points, $\rho$ is blood density, V is average flow velocity, L is the distance between the two measurement points, and D is the diameter of the vessel. Solving for average blood flow velocity:

$$V^2 = \frac{\Delta P}{2\rho f(L/D)} = \frac{\Delta P r_o}{2\rho f \Delta x} \quad (8)$$

Solving Eq. (5) for V gives:

$$V = \frac{q}{\pi r_o^2 \rho} \quad (9)$$

Now substituting Eq. (9) into Eq. (8) and solving for q gives:

$$q^2 = \frac{\pi^2 \rho r_o^5 \Delta P}{2 f \Delta x} \quad (10)$$

Then, solving for q gives:

$$q = \pi \sqrt{\frac{\rho r_o^5}{2f\Delta x}} \sqrt{\Delta P} \qquad (11)$$

Thus, the flow rate q is proportional to the square root of the pressure drop $\Delta P$ in turbulent flow. In measuring aortic blood flow, the proportionality constant is composed of parameters that are essentially fixed for a given patient. Curve 40 of FIG. 4 graphically represents the turbulent flow region defined by Eq. (11).

Figure 4:
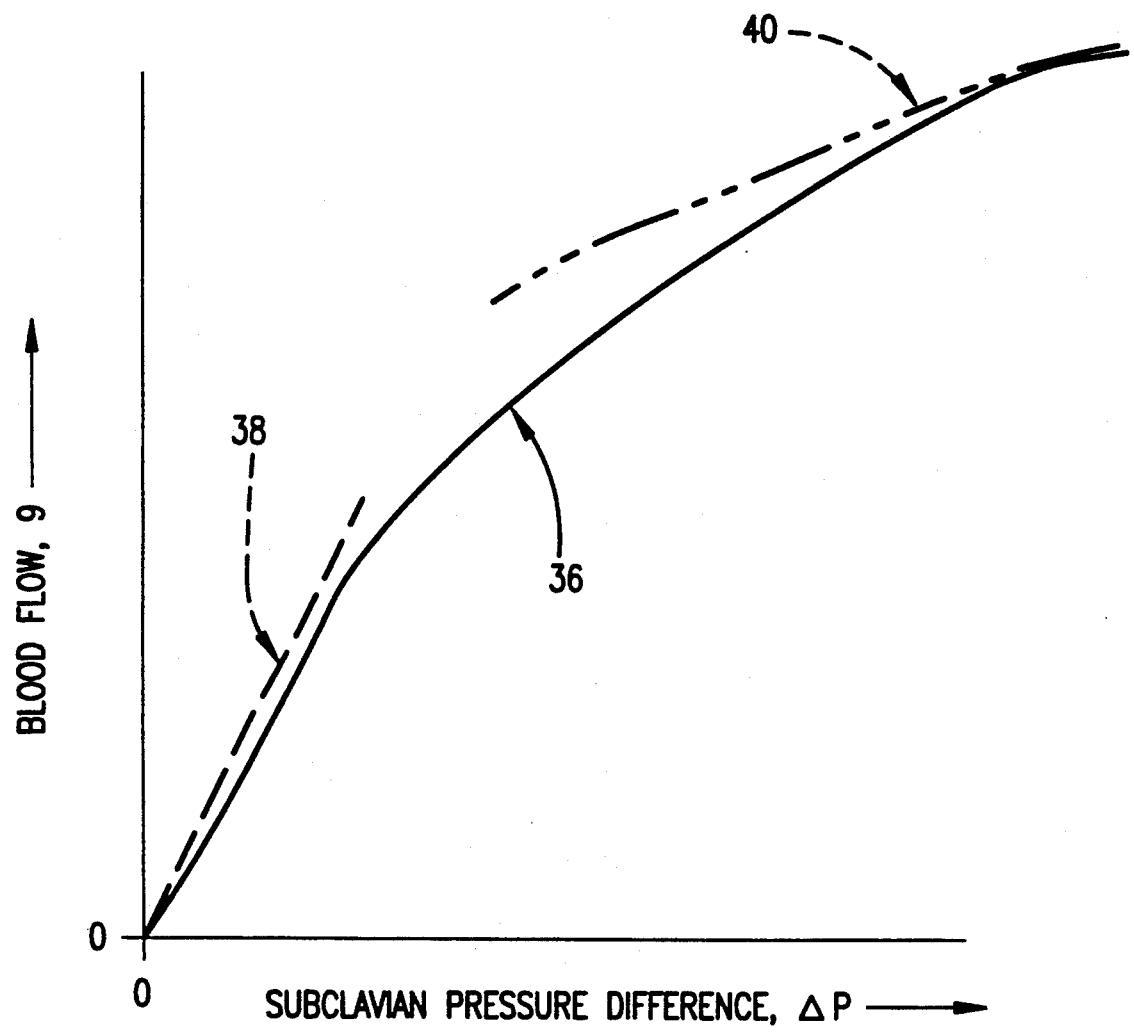
FIG. 4 is a graph showing the pressure/flow relationship.

As shown by curve 38 of FIG. 4, for low velocity laminar flow the flow rate is proportional to $\Delta P$, and the proportionality constant is $\rho \pi r_o^4/8\mu\Delta x$. As shown by curve 40 of FIG. 4, for high velocity turbulent flows the flow rate is proportional to the square root of $\Delta P$ and the proportionality constant is $\pi(\rho r_o^5/2f\Delta x)^{\frac{1}{2}}$. For flow rates lying between these regimes, the behavior is intermediate between the laminar and turbulent flow regimes, as shown by curve 36. The important result is that the flow rate is related in an essentially-fixed, monotonic way to the subclavian pressure difference, $\Delta P$.

The exact shape of the actual aortic pressure/flow curve 36 of FIG. 4 cannot be obtained mathematically with the same ease as the curves in the laminar flow and turbulent flow regions described above. However, it is straightforward to measure the q versus $\Delta P$ relationship either with live patients, with cadavers, or with physical models, fabricated by casting from cadavers. After the q versus $\Delta P$ relationship has been measured for a range of body types and sizes, this information is used in the apparatus of the present invention so that a patient's blood flow can be measured with a fair degree of accuracy. This is accomplished without need to determine the precise q versus $\Delta P$ relationship for that particular patient, simply by using the predetermined stored q versus $\Delta P$ curves. The q versus $\Delta P$ relationship for any particular patient is implemented in the transformation device. The relationship may be implemented using any known means such as by being selected from a stored table provided in a memory means.

It is also useful to note that corrections can be made for curved flow channels. The aorta 10 is certainly curved, so these corrections should ideally be considered in any attempt to derive a q versus $\Delta P$ relationship by analytical methods.

An important aspect of the flow measurement technique described here is that the measurement depends on the (relatively small) difference between two large signals, the equalized and corrected left and right blood pressure signals. A small (percentage) error in either blood pressure signal will lead to a relatively large error in the measurement of blood flow. The various sources of small errors in tonometric blood pressure measurements are well-known. If the offset correction devices 30 are not used, these small errors would be large enough to cause unacceptable errors in the aortic blood flow measurement. Thus, the offset correction devices 30 have an important influence on the accuracy of the measurement system.

Except for certain situations such as vigorous exercise, the aortic blood flow is highly pulsatile, and drops essentially to zero during the later part (i.e., just prior to left ventricle contraction) of the cardiac cycle. This behavior is used by the offset correction devices 30 to correct the sensor signals. During this zero-flow part of the cardiac cycle, the pressures in the two subclavian arteries and 12 will be essentially equal, and hence, their pressure difference should be nearly equal to zero.

As shown in FIG. 2, one of the two offset correction devices 30 is optional. In the most general case, two offset correction devices 30 are used, but one offset correction device 30 is sufficient for most situations. When only one offset correction device 30 is used, the output from one equalization device 28a is input directly to the differential amplifier 32. The operation of the embodiment shown in FIG. 2 will be described for the case of a single offset correction device 30, which is installed in the line carrying the left artery pressure signal.

The sensor control means 26 detects the diastolic and systolic points on the radial blood pressure waveforms. Algorithms to identify these points are wellknown. Based on these identified points, each sensor control means 26 outputs a timing signal 26b that indicates the occurrence of the zero-flow part of the cardiac cycle. For example, let $t_a$ be the running average of the period of the cardiac cycle. Assume the cycle starts at the systolic point of the right radial artery pressure waveform. One algorithm for finding the zero-flow part of the cycle would begin the zero-flow segment at $t \approx (0.8)t_a$ and would end it at a time 4 ms prior to the diastolic point of the right radial artery pressure signal. This algorithm is offered as a good example, but other algorithms may be used without departing from the teachings of this invention.

The timing signals 26b are input to the offset correction device 30. Each offset correction device 30 preferably uses the timing signal 26b from the opposite arm. That is, the first offset device 30 preferably uses the second timing signal 26b, while the second offset correction device (if implemented) preferably uses the first timing signal 26b. Alternatively, each offset correction device 30 uses the same arm timing signal 26b, or uses both timing signals 26b. A second input to each offset correction device 30 is the amplified signal 32a output by the differential amplifier 32. The output of the differential amplifier 32 should be zero during the zero-flow part of the cardiac cycle. This zero-output condition is achieved by operation of the offset correction device 30 as described below.

Figure 3:
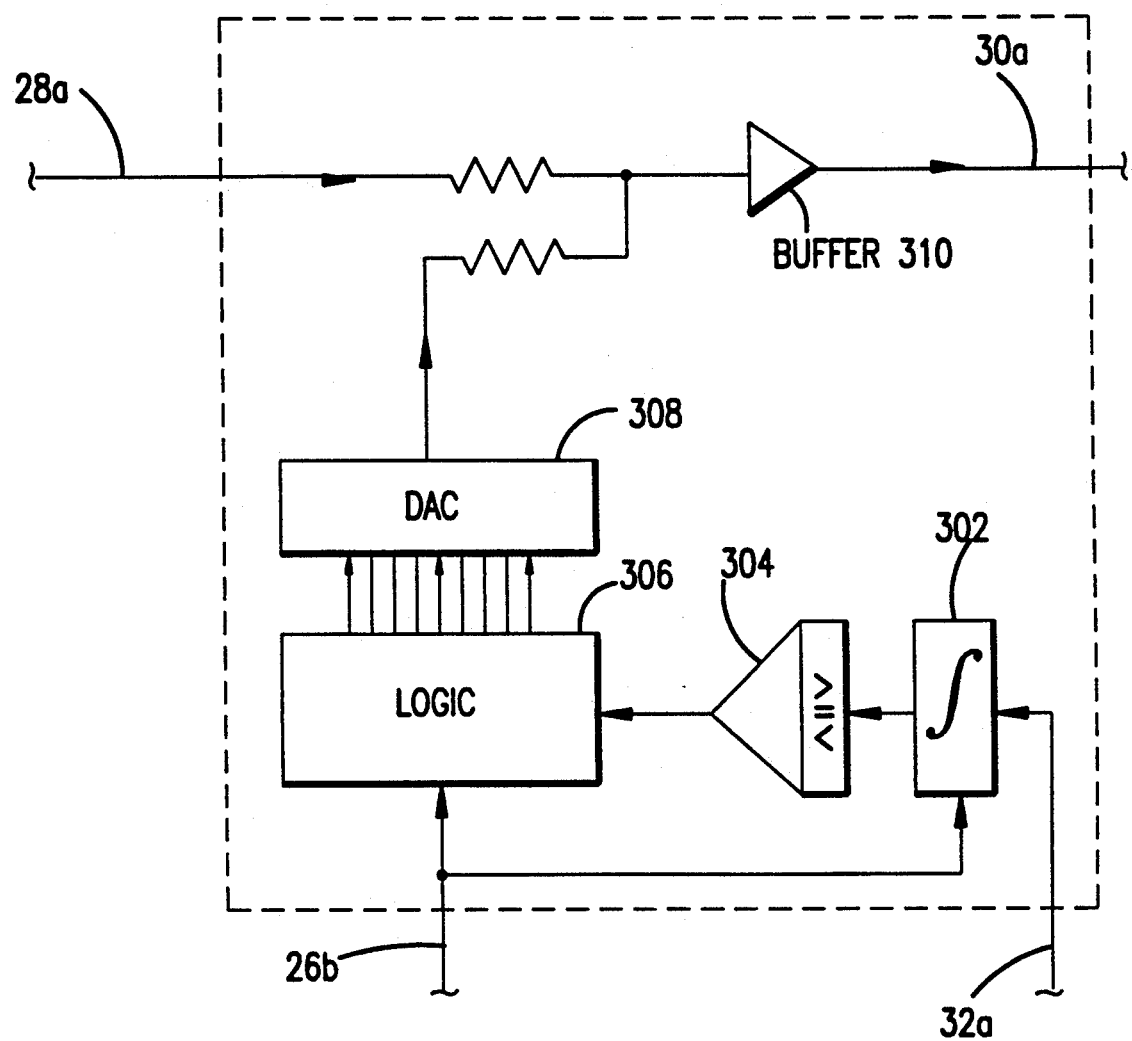
FIG. 3 is a schematic view of the offset correction means.

The operation of the offset correction device 30 can be understood by referring to FIG. 3. FIG. 3 shows the internal components of the offset correction device 30. The amplified signal 32a output by the differential amplifier 32 is input to an integrator circuit 302. This integrator circuit 302 is controlled in the conventional manner by the timing signals 26b. Specifically, the output from integrator circuit 302 is reset to zero just prior to the beginning of the zero-flow time period. During the zero-flow part of the cardiac cycle, as indicated by the timing signals 26b, the integrator circuit 302 integrates the amplified signal 32a and outputs a signal equal to the integral. When the zero-flow time period ends, the integrator circuit 302 ceases to integrate its input, and the level of its output signal is "frozen". This sort of integrator circuit 302 is well-known in the art.

The output signal from the integrator circuit 302 is input to a three-state comparator 304. The three-state comparator 304 has three output states that correspond to the input $\geq$ d, input $\leq$ −d, and d > input > −d, respectively, where d is a threshold voltage In the preferred embodiment, d is chosen to represent a very small pressure—e.g. 0.01 mmHg.

The output signal from the three-state comparator 304 is input to the logic circuit 306 shown in FIG. 3. Second inputs to the logic circuit 306 are the timing signals 26b. The signals output by the logic circuit 306 are input to a digital-to-analog converter (DAC) 308.

Immediately after the end of the zero-flow time period, the logic circuit 306 is activated. First, the logic circuit 306 reads the output from the three-state comparator 304 to determine its state. Then, based on the state of the three-state comparator 304, the logic circuit 306 will execute one of three actions:

1) If the three-state comparator 304 indicates that the integral signal is greater than or equal to d, the output of the logic circuit 306 will be increased by one count.

2) If the three-state comparator 304 indicates that the integral signal is less than or equal to d, the output of the logic circuit 306 will be decreased by one count.

3) If the three-state comparator 304 indicates that the integral signal is between d and −d, the output of the logic circuit 306 will not be changed.

Referring to FIG. 3, the voltage level of the signal output by the DAC 308 is added to the voltage level of the equalized signal 28a, which is input to the offset correction device 30. The equalized signal 28a is the output of the left equalization device 28. The sum signal is buffered by a suitable amplifier 310, and is the output 30a of the offset correction device 30.

It may be seen by consideration of the above description, together with FIGS. 2 and 3, that the offset correction device 30 will act to adjust the DAC 308 out signal to a voltage level that will assure that the voltage 32a is essentially zero during the zero-flow part of the cardiac cycle. Usually, the corrected signal will not "converge" to this state until several seconds or minutes after the blood flow measurement apparatus is connected to the patient. However, once the corrected signal has "converged," it should be relatively stable.

The preferred embodiment of the first offset correction device 30 described above is presented as one example, but other embodiments of offset correction devices 30 may be used without departing from the teachings of this invention. The embodiment of the second offset correction device, when implemented in a two offset correction device apparatus, while not identical to the embodiment of the first offset correction device, follows directly from the embodiment of the first offset correction device.

The aortic blood flow measurement apparatus shown in FIG. 2 forms a feedback-controlled system, and this type of system has been studied extensively by practitioners of control system theory. Numerous variations on the operation and design of the aortic blood flow measurement apparatus will be apparent to those skilled in the art of control system theory. For example, the time required for the system to "converge" can be reduced greatly if the logic circuit 306 and comparator 304 are changed so that the logic circuit 306 output is adjusted by an amount proportional to the integrator 302 output voltage.

The aortic blood flow measurement shown in the apparatus of FIGS. 2 and 3 makes extensive use of analog voltages to represent the blood pressure signals 26a, equalized signals 28a, corrected signals 30a, and flow signals. All the functions and signals of the preferred embodiment shown in FIGS. 2 and 3 may be implemented by using one or more digital computers or microprocessors. Such a digital implementation would not be a departure from the teachings of this invention.

It should also be noted that for optimal operation, the "gain" of the two tonometer sensors 24, after modification, if any, by the associated sensor controller 26, must be approximately equal. Thus, it is recommended that the two sensors 24 be placed at as nearly identical locations on the two arms 22 as possible In addition, if "cuff calibration" is used, any gain adjustment should be applied equally to the two sensors 24.

What is claimed is:

1. A method for measuring blood flow in an aorta of a patient, comprising the steps of:
   determining a first blood pressure in a first subclavian artery of the patient;
   generating a first pressure signal indicative of the first blood pressure;
   determining a second blood pressure in a second subclavian artery of the patient;
   generating a second pressure signal indicative of the second blood pressure;
   removing a DC offset within at least one of the signals,
   generating a difference signal indicative of a difference between the first pressure signal and the second pressure signal; and
   generating a flow signal indicative of the blood flow in the aorta from the difference signal.

2. The method of claim 1, wherein the steps of determining the first and second pressure signals comprise:
   measuring a first blood pressure in an artery of a first arm of the patient;
   measuring a second blood pressure in a corresponding artery of a second arm of the patient; and
   applying equalization to the first and second arm artery pressures.

3. The method of claim 2, wherein the artery is one of a brachial artery, a radial artery, an ulnar artery and a finger artery of the first arm and the corresponding artery is one of a brachial artery, a radial artery, an ulnar artery and a finger artery of the second arm.

4. The method of claim 3, wherein the artery is the radial artery of the first arm and the corresponding artery is the radial artery of the second arm.

5. The method of claim 2, wherein the steps of measuring the first blood pressure and the second blood pressure use a first and a second arterial tonometric blood pressure sensor, respectively.

6. The method of claim 5, further comprising the step of calibrating the tonometric measurements using at least one blood pressure cuff.

7. The method of claim 2, wherein the step of applying equalization to the first and second arm artery pressure signals comprises the steps of:
   determining a first transfer function for the first pressure signal and a second transfer function for the second pressure signal;
   applying equalization to the first pressure signal based on the first transfer further; and
   applying equalization to the second pressure signal based on the second transfer function.

8. The method of claim 7, wherein the step of determining the first and second transfer functions uses previous measurements of typical patients.

9. The method of claim 7, further comprising selecting the first and second transfer functions based on at least one of an age, a height, a sex, and a weight of the patient.

10. The method of claim 1, wherein the step of removing the DC offset comprises:

determining a first diastolic point and a first systolic point on the first blood pressure signal;
determining a zero-flow period of the first pressure signal from the first diastolic and first systolic points;
determining an average value of the difference signal during the zero-flow period; and
altering the first pressure signal based on said average value of the difference signal.

11. The method of claim 10, further comprising the steps of:
integrating the difference signal during the zero-flow period and generating an integral signal;
holding a value of the integral signal at an end of the zero-flow period;
generating a comparison result based on the held value of the integral signal;
altering an offset signal based on the comparison result; and
adding said offset signal to the first pressure signal.

12. The method of claim further comprising the steps of:
determining a second diastolic point and a second systolic point of the second pressure signal;
determining a second zero-flow period of the second pressure signal from the second diastolic and systolic points;
determining a second average value of the difference signal during the second zero-flow period; and
altering the second pressure signal based on the said second average value.

13. The method of claim 12, further comprising the steps of:
integrating the difference signal during the zero-flow period and generating an integral signal;
holding a value of the integral signal at an end of the zero-flow period;
generating a comparison result based on the held value of the integral signal;
altering an offset signal based on the comparison result; and
adding said offset signal to the second pressure signal.

14. The method of claim 1, wherein the step of generating a signal indicative of the aortic blood flow comprises the steps of:
determining a pressure/flow relationship between the difference signal and the blood flow; and
generating the flow signal based on the difference signal and the pressure/flow relationship.

15. The method of claim 14, wherein the step of determining the pressure/flow relationship in a laminar region of the pressure/flow relationship is given by the equation:

$$q = (-\rho \pi r_o^4 / 8\mu \Delta x)\Delta P$$

where:
q is the flow rate signal;
$\Delta P$ is the pressure difference signal;
$\rho$ is the blood density;
$r_o$ is the internal radius of the aorta;
$\mu$ is the blood viscosity; and
$\Delta x$ is the distance between junctions of the subclavian arteries and the aorta.

16. The method of claim 14, wherein the step of determining the pressure/flow relationship in a turbulent region of the pressure/flow relationship is given by the equation:

$$q = \pi(\rho r_o^5 / 2f\Delta x)^{\frac{1}{2}} (\Delta P)^{\frac{1}{2}}$$

where:
q is the flow rate signal;
$\rho$ is the blood density;
f is the friction factor;
$\Delta P$ is the pressure difference signal;
$r_o$ is the internal radius of the aorta; and
$\Delta x$ is the distance between junctions of the subclavian arteries and the aorta.

17. An apparatus for non-invasively measuring blood flow in an aorta of a patient, comprising:
a first sensor means for measuring a first blood pressure and generating a first sensor signal;
a second sensor means for non-invasively measuring a second blood pressure and generating a second sensor signal; and
a control means for generating a flow signal indicative of blood flow in the aorta based on the first and second sensor signals.

18. The apparatus of claim 18, wherein the first and second sensor means comprise tonometric blood pressure sensors.

19. The apparatus of claim 17, wherein the first and second sensor means measure the first and second blood pressures, respectively, in an artery of a first arm and in a corresponding artery of a second arm of the patient.

20. The apparatus of claim 19, wherein the first and second sensor means measure the first and second sensor signals in one of a brachial artery, a radial artery, an ulnar artery and a finger artery.

21. The apparatus of claim 19, wherein the first and second sensor means measure the first blood pressure and the second blood pressure such that the first and second blood pressures are indicative of blood pressure in a first and a second subclavian artery, respectively.

22. The apparatus of claim 17, wherein the first sensor means further comprises a first sensor controller connected to the a first sensor for generating a first blood pressure signal from the first sensor signal, for controlling the first sensor and for generating a first timing signal from the first blood pressure signal; and
the second sensor means comprises a second sensor controller connected to a second sensor for generating a second blood pressure signal from the second sensor signal, for controlling the second sensor, and for generating a second timing signal from the second blood pressure signal; and
the control means further comprises:
a first equalization means connected to the first sensor controller for generating a first equalized signal from the first blood pressure signal;
a second equalization means connected to the second sensor controller for generating a second equalized signal from the second blood pressure signal; and
a first offset correction means connected to the first equalization means and to at least one of the first and second sensor controllers for generating a first corrected signal by removing a DC offset from the first equalized signal based on at least one of the first and the second timing signals.

23. The apparatus of claim 22, wherein the first and second equalization means generate the first and second equalized signals from the first and second blood pressure signals based on a first and a second transfer function, respectively.

24. The apparatus of claim 23, further comprising means for determining the first and second transfer functions from previous measurements of typical patients.

25. The apparatus of claim 23, further comprising means for determining the first and second transfer functions from at least one of an age, a height, a weight, and a sex of the patient.

26. The apparatus of claim 22, wherein the control means further comprises:
- a first difference means connected to the first offset correction means and the second equalization means for generating a difference signal from the first corrected signal and the second equalized signal; and
- a pressure/flow conversion means for converting the difference signal to a flow signal.

27. The apparatus of claim 26, wherein the first offset correction means is connected to at least one of the first sensor controller and the second sensor controller, the first equalization means, and the first difference means, and the offset correction means comprises:
- integrator means for generating an integral signal from the difference signal and at least one of the first timing signal and the second timing signal, and holding a final integrated value of the integral signal;
- comparison means for comparing the final integrated value to a predetermined threshold value, and for generating a comparison result signal;
- logic device means for generating an offset signal based on the comparison result signal;
- means for summing the offset signal and the first equalized signal and generating the first corrected signal.

28. The apparatus of claim 26, wherein the pressure/flow conversion means converts the difference signal to the flow signal based on a predetermined pressure/flow relationship.

29. The apparatus of claim 22, wherein the control means further comprises:
- a second offset correction means connected to the second equalization means and at least one of the first and second sensor controllers for generating a second corrected signal by removing a D.C. offset from the second equalized signal based on at least one of the first and second timing signals;
- a first difference means connected to the first and second offset correction means for generating a difference signal from the first and second corrected signals; and
- a pressure/flow conversion means for converting the difference signal to a flow signal.

30. The apparatus of claim 29, wherein the pressure/flow conversion means converts the difference signal to the flow signal based on a predetermined pressure/flow relationship.

* * * * *